United States Patent [19]

Habermeier et al.

[11] 4,038,277
[45] July 26, 1977

[54] MONO- AND DIALCOHOLS OF FIVE OR SIX MEMBERED N-HETEROCYCLIC COMPOUNDS, CONTAINING TWO NH GROUPS PER MOLECULE

[75] Inventors: Juergen Habermeier, Allschwil; Hans Batzer, Arlesheim; Daniel Porret, Binningen, all of Switzerland

[73] Assignee: Ciba-Geigy AG, Basel, Switzerland

[21] Appl. No.: 577,965

[22] Filed: May 15, 1975

Related U.S. Application Data

[63] Continuation of Ser. No. 82,072, Oct. 19, 1970, abandoned, which is a continuation-in-part of Ser. No. 1,289, Jan. 7, 1970, Pat. No. 3,679,681.

[30] Foreign Application Priority Data

Jan. 24, 1969 Switzerland .......................... 1104/69

[51] Int. Cl.$^2$ .................... C07D 239/54; C07D 233/72
[52] U.S. Cl. .......................... 260/256.4 C; 260/309.5
[58] Field of Search .............. 260/260, 309.5, 256.4 C

*Primary Examiner*—Paul M. Coughlan, Jr.
*Attorney, Agent, or Firm*—Vincent J. Cavalieri

[57] ABSTRACT

New mono- and dialcohols of binuclear, five-membered or six-membered, unsubstituted or substituted N-heterocyclic compounds, which contain two NH groups in the molecule, by reaction of binuclear, five-membered or six-membered, unsubstituted or substituted, N-heterocyclic compounds, such as bis-(hydantoin) or bis-(dihydrouracil) compounds, for example 1,1′-methylene-bis-(5,5-dimethylhydantoin), bis-(5,5-dimethylhydantoinyl-3)-methane or 1,1′-methylene-bis-(5,6-dihydrouracil) with ethylene oxide, for example ethylene oxide or propylene oxide, to give the corresponding monohydroxy or dihydroxy compounds. These compounds are useful as intermediates for forming diglycidyl ether resins as described in German Offenlegungsschrift No. 2,003,016.

11 Claims, No Drawings

MONO- AND DIALCOHOLS OF FIVE OR SIX MEMBERED N-HETEROCYCLIC COMPOUNDS, CONTAINING TWO NH GROUPS PER MOLECULE

This is a continuation of application Ser. No. 82,072 filed on Oct. 19, 1970, now abandoned which is a continuation-in-part application of application Ser. No. 1289, filed Jan. 7, 1970, now U.S. Pat. No. 3,679,681.

The subject of the present invention are new mono- and dialcohols of the general formula:

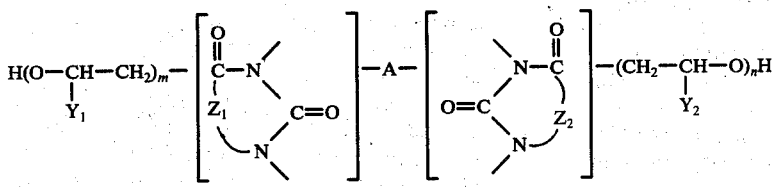

wherein $Z_1$ and $Z_2$ independently of one another each denote a nitrogen-free divalent residue which is required for completing a five-membered or six-membered, unsubstituted or substituted, heterocyclic ring, A represents a divalent aliphatic, cycloaliphatic or araliphatic residue, and in particular preferably an alkylene residue or an alkylene residue which is interrupted by oxygen atoms, $Y_1$ and $Y_2$ each denotes a hydrogen atom or a methyl group and $m$ and $n$ each represents an integer having a value of 0 to 30, preferably of 0 to 4, with the sum of $m$ and $n$ having to be at least 1.

The residues $Z_1$ and $Z_2$ in the formula (I) preferably consist only of carbon and hydrogen or of carbon, hydrogen and oxygen. Each can for examle be one of the residues of formulae

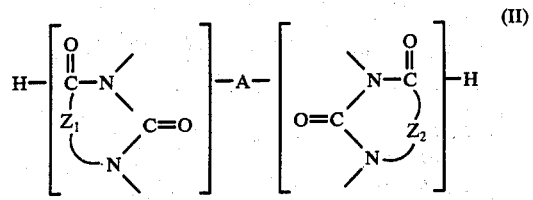

wherein R', R'', R''' and R'''' independently of one another each can denote a hydrogen atom or, for example, an alkyl residue, an alkenyl residue, a cycloalkyl residue or an optionaly substituted phenyl residue.

The new mono- and dialcohols of formula (I) can be manufactured by reacting binuclear N-heterocyclic compounds of general formula

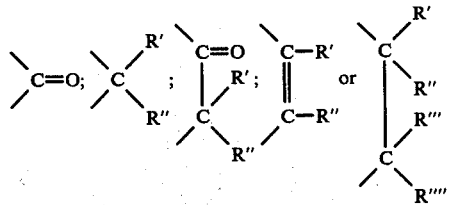

wherein $Z_1$, $Z_2$ and A have the same significance as in formula (I), with alkene oxides vix. ethene oxide (ethylene oxide) and propene oxide (propylene oxide), preferably in the presence of a suitable catalyst.

The addition of an alkene oxide to one or both NH groups of the binuclear N-heterocyclic compounds of formula (III) can be carried out both in the presence of acid catalysts and of alkaline catalysts, with a slight excess over the equivalent of the alkylene oxide being employed per equivalent NH group of the binuclear N-heterocyclic compound of formula (III).

Preferably, however, alkaline catalysts, such as tetraethylammonium chloride or tertiary amines, are used in the manufacture of monoalcohols and dialcohols of formula (II) in which the sum of $m$ and $n$ is 1 or 2. However, alkali metal halides such as lithium chloride or sodium chloride can also be successfully used for this addition reaction; it also takes place without catalysts.

In the manufacture of dialcohols of formula (II) in which the sum of $m$ and $n$ is greater than 2, it is preferable to start from the simple dialcohols of formula (II) in which $m$ and $n$ are each 1, and to add further alkene oxide to both OH groups of this compound in the presence of acid catalysts.

Suitable acid catalysts for this addition reaction are particularly Lewis acids, such as for example $AlCl_3$, $SbCl_5$, $SnCl_4$, $FeCl_3$, $ZnCl_2$, $BF_3$ and their complexes with organic compounds.

The binuclear N-heterocyclic compounds of formula (II) used for the manufacture of the new alkene oxide addition products of formula (I) are above all bis-(hydantoin) compounds or bis-(dihydrouracil)*compounds in which the two N-heterocyclic rings are linked to one another via an alkylene bridge, for example a methylene group, which is bonded to an endocyclic nitrogen atom of each of the heterocyclic rings in question.

A first category of such bis-(hydantoin) compounds corresponds to the general formula

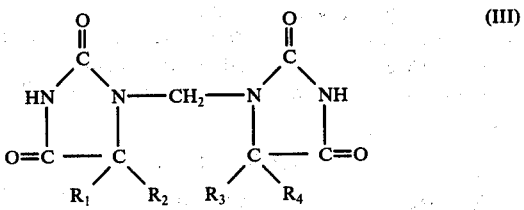

wherein $R_1$, $R_2$, $R_3$ and $R_4$ each denote a hydrogen atom or a lower alkyl residue with 1 to 4 carbon atoms, or wherein $R_1$ and $R_2$, and/or $R_3$ and $R_4$, together form a tetramethylene or pentamethylene residue.

There may for example be mentioned 1,1'-methylene-bis-(5,5-dimethyl-hydantoin), 1,1'-methylene-bis-(5-methyl-5-ethyl-hydantoin), 1,1'-methylene-bis-(5-propyl-hydantoin) and 1,1'-methylene-bis-(5-isopropyl-hydantoin).

A further category of such bis-(hydantoin) compounds corresponds to the general formula

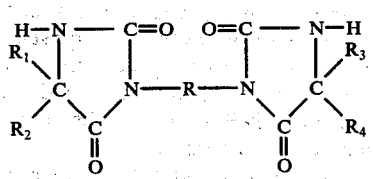

wherein R is an aliphatic, cycloaliphatic or araliphatic residue, especially an alkyl residue or an alkylene residue interrupted by oxygen atoms, and R, $R_2$, $R_3$ and $R_4$ each denote a hydrogen atom or a lower alkyl residue with 1 to 4 carbon atoms, or wherein $R_1$ and $R_2$ and/or $R_3$ and $R_4$ together form a tetramethylene or pentamethylene residue. Bis-(5,5-dimethyl-hydantoinyl-3)-methane, 1,2-bis-(5',5'-dimethyl-hydantoinyl-3')-ethane, 1,4-bis-(5',5'-dimethyl-hydantoinyl-3')-butane, 1,6-bis-(5',5'-dimethyl-hydantoinyl-3')-hexane, 1,12-bis-(5',5'-dimethyl-hydantoinyl-3')-dodecane and β,β'-bis-(5',5'-dimethylhydantoinyl)-3')-diethyl-ether may be mentioned.

A preferentially used category of bis-(dihydrouracil) compounds corresponds to the general formula

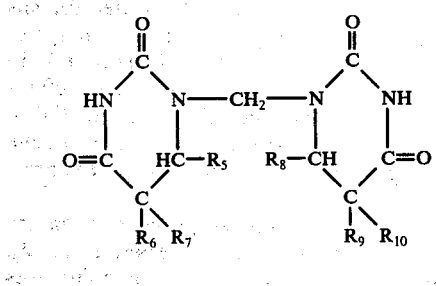

wherein $R_5$, $R_6$, $R_7$, $R_8$, $R_9$ and $R_{10}$ independently of one another each denote a hydrogen atom or a lower alkyl residue with 1 to 4 carbon atoms.

1,1'-Methylene-bis-(5,6-dihydrouracil), 1,1'-methylene-bis-(6-methyl-5,6-dihydrouracil) and 1,1'-methylene-bis-(5,5-dimethyl-5,6-dihydrouracil) may be mentioned.

EXAMPLE 1

A mixture of 529 g of ethylene oxide (12 mols) and 1 liter of dimethylformamide, cooled to 5° C, is added to a mixture of 1341.5 g of 1,1'-methylene-bis-(5,5-dimethylhydantoin) [5 mols], 3 liters of dimethylformamide and 12.5 g of lithium chloride at room temperature. The mixture is heated to 75° C over the course of 1 hour and 45 minutes with good stirring, and the reaction then starts to become weakly exothermic. The reaction temperature is kept for 3½ hours at 75°-78° C and the mixture is subsequently stirred for a further 2 hours at 100°-105° C. The hot solution is filtered off, neutralised with 20% strength sulphuric acid and subjected to a vacuum distillation. The dimethylformamide is largely distilled off at 100° C bath temperature and 15 mm Hg and a crystalline residue is obtained. This crude product was recrystallised from a three-fold amount of dioxan, and dried. 1462 g (corresponding to 81.4% of theory) of pure 1,1'-methylene-bis-(3-β-hydroxyethyl-5,5-dimethylhydantoin) of melting point 165°-165.7° C are obtained in the form of colourless glistening crystals. Elementary analysis shows:

| found | calculated |
|---|---|
| 50.68 % C | 50.55 % C |
| 6.69 % H | 6.79 % H |
| 15.58 % N | 15.72 % N |

The molecular weight was determined to be 359 (theory: 356.4) by vapour pressure osmometry, and analysis by gel permeation chromatography shows that a substance of uniform molecular weight is present. The IR-(infrared) spectrum shows, through the absence of the NH-amide absorptions and the C—O—C absorption at 9.0-9.3 μ and through the presence of the OH absorptions at 2.95-3.0 μ that the desired substance has been produced. The H—NMR (nuclear magnetic resonance) spectrum shows, through the presence of the following protons, that the structural formula given below is applicable:

12 protons (CH$_3$) at δ = 1.38
8 protons (CH$_2$) at δ = 3.49
2 protons (—OH) at δ = 4.68
2 protons (N—CH$_2$—N) at δ = 4.95

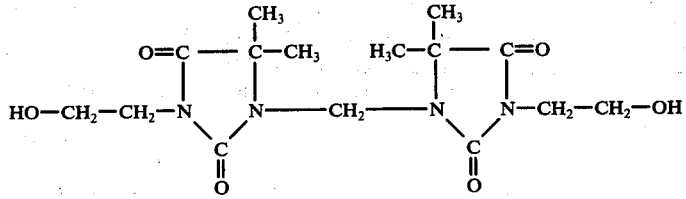

EXAMPLE 2

3.0 ml of 48% strength boron trifluoride-diethyl etherate solution (in diethyl ether) are added at 65° C to a solution of 178.0 g of 1,1'-methylene-bis-(3-β-hydroxyethyl-5,5-dimethylhydantoin) [0.5 mol] (manufactured according to Example A) in 700 ml of dioxan. Thereafter 44.8 liters of gaseous ethylene oxide (2 mols) are passed into the solution over the course of 4 hours whilst stirring; the amount of ethylene oxide introduced is controlled with the aid of a gas flow meter (Rotameter). The reaction is weakly exothermic and the reaction mixtue becomes warmed to 73° C.

After completion of the introduction of the ethylene oxide, the mixture is stirred for a further 3 hours at 75° C and is then adjusted to pH 7 with finely powdered potassium carbonate, and filtered. The clear filtrate is concentrated on a rotary evaporator and is then dried to constant weight (100° C, 0.1 mm Hg).

265 g (100% of theory) of an ochre-coloured viscous resin are obtained, the H—NMR (nuclear magnetic resonance) spectrum of which shows the presence of 40 protons; the molecular weight is 505 ± 25 (theory 532).

This shows that mainly the following product has been produced:

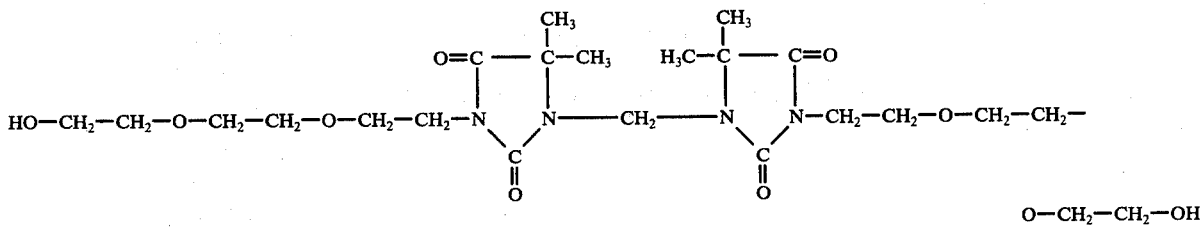

EXAMPLE 3

A mixture of 258.3 g of 1,1'-methylene-bis-(5,5-dimethylhydantoin) [1 mol], 600 ml of dimethylformamide and 2.11 g of lithium chloride is stirred at 60° C. 134.0 g of propene oxide (2.3 mols) are slowly added dropwise to this mixture over the course of 1 hour and 45 minutes. Thereafter the mixture is heated to 100° C over the course of 1.5 hours and stirred at 100° C for a further 2 hours. The hot reaction mixture is now filtered and cooled to room temperature, neutralized with 20% strength sulphuric acid and concentrated to dryness on a rotary evaporator. The crude product is recrystallised from ethanol. 327.0 g of pure 1,1'-methylene-bis-(3-β-hydroxy-n-propyl-5,5-dimethylhydantoin) [85.3% of theory] of melting point 131°-133° C are obtained. Microanalysis above 14.50% N (calculated, 15.58% N); analysis by gel permeation chroaamatography shows that the substance is of uniform molecular weight. The N—NMR (nuclear magnetic resonance) spectrum and the IR (infrared) spectrum can be reconciled with the following structures:

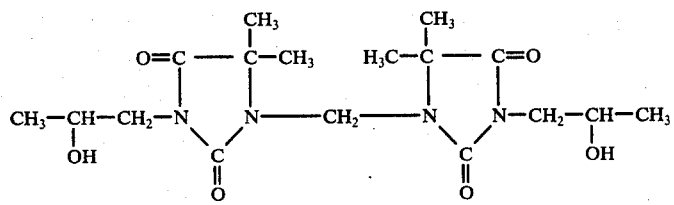

EXAMPLE 4

88.9 g of 1,1'-methylene-bis-(5,5-dimethyl-5,6-dihydrouracil) and 0.63 g of lithium chloride in 300 ml of dimethylformamide are reacted with a solution of 29.4 g of ethylene oxide in 150 ml of dimethylformamide according to the method described in Example A. After working up according to Example A, a high viscous practically colourless reaction product is obtained in 100% yield (115 g). The product can be purified by reprecipitation from methanol/water. The H—NMR (nuclear magnetic resonance) spectrum shows the presence of 28 protons and agrees with the structure given below. The molecular weight is determined by vapour pressure osmometry to be 382 (theory 384.3).

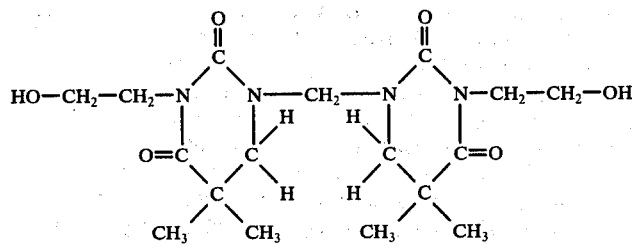

EXAMPLE 5

A solution of 88.1 g of ethylene oxide (2 mols) moles) in 300 ml of dimethylformamide is reacted, according to the method described in Example A, with a mixture of 155.2 g of 1,4-bis-(5',5'-dimethylhydantoinyl-3')-butane (0.5 mol), 2.12 g of lithium chloride and 700 ml of dimethylformamide, but the reaction time is here 24 hours. The mixture is worked up according to Example A and 199 g of crystalline crude 1,4-bis-(1'-β'-hydroxyethyl-5',5'-dimethylhydantoinyl-3')-butane (100% of theory) are obtained. The crude product is purified by recrystallisation from methanol. After drying at 90° C/150 mm Hg, 144.2 g of pure product of melting point 173°-175° C are obtained. Elementary analysis shows:

| found | calculated |
|---|---|
| 54.07 % C | 54.26 % C |
| 7.64 % H | 7.59 % H |
| 14.03 % N | 14.08 % N |

The determination of the molecular weight by vapour pressure osmometry shows = 398 (theory = 398.4). Analysis by gel permeation chromatography shows that the product has a uniform molecular weight. IR (infrared) and N—NMR (nuclear magnetic resonance) spectra prove the following structure:

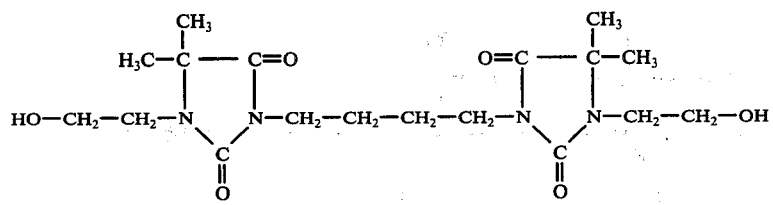

Example 6

A solution of 88.1 g of ethylene oxide (2 mols) in 300 ml of dimethylformamide is mixed, in accordance with the method described in Example A, with a mixture of 169.5 g of 1,6-bis-(5,5'-dimethylhydantoinyl-3')-hexane (0.5 mol), 2.12 g of lithium chloride (10 mol percent relative to the hydantoin derivative) and 700 ml of dimethylformamide and warmed to 75° C over the course of 1 hour. The mixture is stirred for 17 hours at 75° C and then for a further 5 hours at 100° C. The reaction mixture is filtered, adjusted to pH=7 with 20% strength sulphuric acid and evaporated to dryness on a rotary evaporator at 100° C/15 mm Hg. 214 g of crude product (100% of theory) are obtained in the form of a brown viscous oil which crystallises out on standing. For purification, the crude product is very intensively stirred with 1 liter of diethyl ether, filtered off from the brown solution and dried, 189 g (= 88.8% of theory) of 1,6-bis-(1',β'-hydroxyethyl-5',5'-dimethylhydantoinyl-3')-hexane are obtained in the form of fine almost colourless crystals of melting point 89°–92° C. The H—NMR (nuclear magnetic resonance) spectrum shows the presence of 30 protons, which agrees with theory. The IR spectrum shows the following absorptions:

2.86 μ (s) [OH]
5.67 μ (s) [C=O]
5.87 μ (ss) [C=O]
furthermore: 7.60μ; 7.85 μ; 8.06 μ; 8.53 μ; 8.85 μ; 9.05 μ; 9.46 μ; 10.22 μ; 11.12 μ; 11.95 μ; 13.02 μ; 13.40 μ; 14.18 μ.

Accordingly, the product has the following structure:

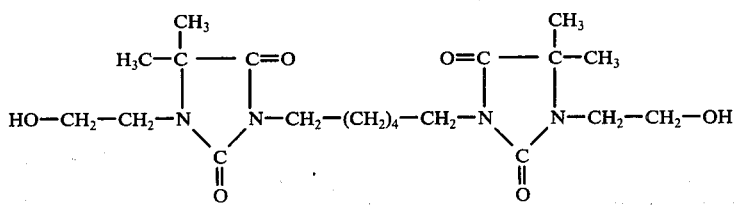

EXAMPLE 7

116.2 g of propene oxide are added dropwise over the course of 6 hours, whilst stirring, to a solution of 169.5 g of 1,6-bis-(5=,5'-dimethylhydantoinyl-3')-hexane, 106 g of lithium chloride and 1 liter of dimethylformamide warmed to 75° C. Thereafter the mixture is stirred for a further 5 hours at 105° C and subsequently cooled to room temperature and neutralised with concentrated sulphuric acid (about 18 drops are required). The mixture is filtered and the clear colourless filtrate is concentrated to constant weight at 100° C/15 mm Hg. 202 g of a clear pale yellow very viscous melt (89% of theory) are obtained. The H—NMR (nuclear magnetic resonance) spectrum shows inter alia through the presence of 3 different signls for methyl protons

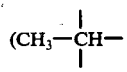

at δ = 1.05 and 1.14;

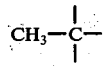

at δ = 1.30), that essentially the following substance, 1,6-bis-(1',β'-hydroxy-n-propyl-5',5'-dimethylhydantoinyl-3')-hexane, is present.

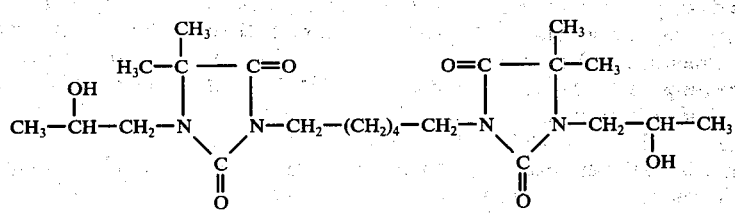

EXAMPLE 8

123.9 g of bis-(5,5-dimethylhydantoinyl-3)-tetrachloro-p-xylylene (0.5 mol), 1.5 l of dimethylformamide and 0.3 g of lithium chloride are stirred at 50° C. 58.1 g of propene oxide (1.0 mol) are slowly added dropwise over the course of 2½ hours. A clear pale yellow solution is produced which is brought to 88°–90° C over the course of 2½ hours. After 8 hours stirring at 88°–90° C the solution is cooled to room temperature and filtered. The filtrate is concentrated to dryness on a rotary evaporator and is subsequently dried to constant weight at 80° C bath temperature under 0.1 mm Hg. 138.7 g of a whitish-yellow crystalline mass (92% of theory) are obtained. The substance melts at 272°-275° C. The infrared spectrum (Nujol paste) shows, through the presence of the absorption at 3500 cm⁻¹, that the structural elements C—OH is present.

EXAMPLE 9

73.0 g of 1,1′-methylene-bis-(3-β-hydroxyethyl-5,5-dimethylhydantoin) [0.205 mol] (manufactured according to Example A) are dissolved in 500 ml of dioxane and stirred at 75° C. 3.5 ml of 47% strength boron fluoride-diethyl etherate solution in ether are added and the introduction of a vigorous stream of ethylene oxide is immediately started. The apparatus is provided with a low temperature condenser so that no ethylene oxide can escape. The ethylene oxide mixture is metered into the apparatus via a gas flow meter (Rotameter). The reaction is immediately exothermic. The heating bath is removed so that the apparatus is cooled by the surrounding air. The strength of the stream of ethylene oxide is made such that the temperature of the mix is 72°-77° C. After 3 hours the supply of ethylene oxide is terminated, the mixture is cooled to room temperature, and 15 ml of 30% strength sodium hydroxide solution and 200 ml of water are stirred in. The whole is filtered and the solution is concentrated on a rotary evaporator at 70° C under a slight vacuum. Thereafter the residue is dried at 90° C bath temperature/0.1 mm Hg.

175.0 g of a liquid, colourless, clear substance are obtained. The weight increase attributable to the ethylene oxide is, accordingly, 102.0 g (2.32 mols), that is to say 5.65 molecules of ethylene oxide have reacted per OH group of the starting substance. The infrared spectrum shows, in addition to the absorptions known from 1,1′-methylene-bis-(3-β-hydroxyethyl-5,5-dimethylhydantoin), a very intense C—O—C absorption at 1124 cm⁻¹. The proton-magnetic resonance spectrum (60 Mc H—NMR, recorded in CDCl₃ with tetramethylsilane as an internal standard) shows the following 4 signals

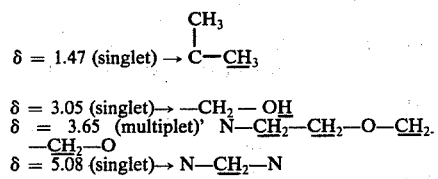

At the same time the integration ratio of the methylene group signal to the signals at δ = 3.65 shows that per N-atom δ 6.7 mols of ethylene oxide have been added on. This agrees well with the gravimetrically determined ratios. Accordingly the substance has the following average structure:

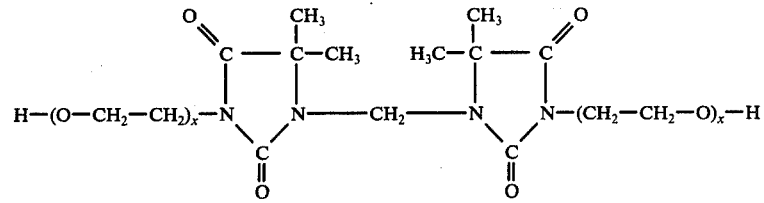

x ≈ 6.7 (average value)

EXAMPLE 10

A mixture of 148.2 g of 1,1′-methylene-bis-(5-isopropylhydantoin) (0.5 mol), 300 ml of dimethylformamide and 1.3 g of lithium chloride is stirred at 50° C. 81.4 g of propene oxide (1.4 mol) are added dropwise over the course of 2 hours whilst stirring. Thereafter the mixture is stirred for a further 10 hours at 80° C, and is cooled to room temperature and filtered. The clear colourless solution is concentrated at 60°-80° C on a rotary evaporator under a waterpump vacuum and is subsequently dried to constant weight at 80°-90° C under 0.1 mm Hg. A clear colourless resin (2.06.3 g) is obtained in 100% yield, which on standing gradually solidifies to give colourless crystals. The infrared spectrum shows, in addition to the absorptions of the 1,1′-methylene-bis-(5-isopropylhydantoin) skeleton, a relatively intense absorption at 3490 cm⁻¹, which is attributable to the C—OH group.

The proton-magnetic resonance spectrum (60 Mc H—NMR, recorded in CDCl₃ at 35° C with tetramethylsilane as an internal standard) shows, through the integration ratio of the signals

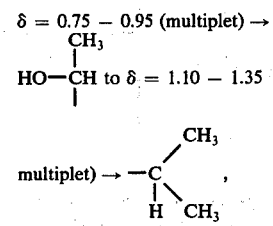

that the addition of propene oxide to the binuclear heterocyclic system in the ratio of 2:1 has taken place quantitatively.

EXAMPLE 11

A solution of 88.9 g of 1,1′-methylene-bis-(5,5-dimethyl-5,6-dihydrouracil) [0.3 mol] and 0.630 g of lithium chloride in 550 ml of dimethylformamide is stirred at 65° C. 38.4 g of propene oxide (0.66 mol) are slowly added dropwise over the course of 2 hours whilst stirring. Thereafter the reaction mixture is heated to 100° C over the course of 30 minutes. The mix is when stirred for a further 5 hours at this temperature, and is then filtered and concentrated at 80° C/40 mm Hg; thereafter it is dried to constant weight at 95° C/0.1 mm Hg.

121.1 g of a completely colourless clear, transparent, glass-like viscous substance (97.8% of theory) are obtained. The infrared and nuclear resonance spectrum show that the grouping

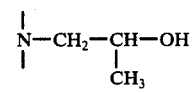

is present nd that only traces of the grouping

are still present.

We claim:

1. A mono-or dialcohol of the formula

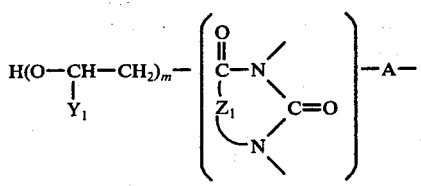

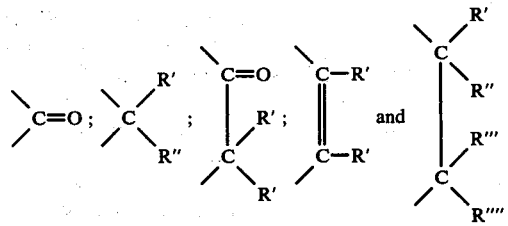

wherein $Y_1$ and $Y_2$ each represents a member selected from the group consisting of hydrogen and methyl, A represents alkylene containing from 1 to 12 carbon atoms, diethylene ether or tetrachloro-p-xylene and $Z_1$ and $Z_2$ each represents a member selected from the group consisting of a divalent residue of the formulae

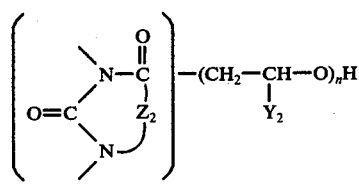

wherein R', R", R'" and R"" each represents a member selected from the group consisting of alkyl with 1 to 5 carbon atoms, alkenyl with up to 5 carbon atoms, cyclohexyl, cyclohexenyl, phenyl, or when the residue $Z_1$ and $Z_2$ represents the formula

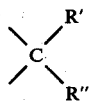

wherein R' and R" together can also form a member selected from the group consisting of tetramethylene and pentamethylene, and m and n each represents an integer having a value of from 0 to 6.7 (average value) with the sum of m and n having to be at least 1.

2. A compound as claimed in claim 1, wherein in the formula I m and n each represents an integer having a value of 0 to 4 with the sum of m and n having to be at least 1.

3. A compound as claimed in claim 1 which is 1,1'-Methylene-bis-(3-β-hydroxyethyl-5,5-dimethylhydantoin).

4. A compound as claimed in claim 1 which is 1,1'-Methylene-bis-(3β-hydroxyethoxyethoxyethyl-5,5-dimethylhydantoin).

5. A compound as claimed in claim 1 which is 1,1'-Methylene-bis-(3-β-hydroxy-n-propyl-5,5-dimethylhydantoin).

6. A compound as claimed in claim 1 which is 1,1'-Methylene-bis-(3-β-hydroxyethyl-5,5-dimethyl-5,6-dihydrouracil).

7. A compound as claimed in claim 1 which is 1,4-Bis-(1'-β'-hydroxyethyl-5',5'-dimethylhyantoinyl-3')-butane.

8. A compound as claimed in claim 1 which is 1,6-Bis-(1'-β'-Hydroxyethyl-5',5'-dimethylhydantoinyl-3')-hexane.

9. A compound as claimed in claim 1 which is 1,6-Bis-(1'-β-hydroxy-n-propyl-5',5'-dimethylhydantoinyl3')-hexane.

10. A compound as claimed in claim 1 which is 1,1'-Methylene-bis-(3-β-hydroxypropyl-5-isopropylhydantoin).

11. A compound as claimed in claim 1 which is 1,1'-Methylene-bis-(3β-hydroxy-n-propyl-5,5-dimethyl-5,6-dihydrouracil).

* * * * *